United States Patent [19]

Hossler

[11] Patent Number: 4,699,130

[45] Date of Patent: Oct. 13, 1987

[54] MODULAR SPLINT SYSTEM

[76] Inventor: Phillip Hossler, 20 Liverpool Ct., Jackson, N.J. 08527

[21] Appl. No.: 887,424

[22] Filed: Jul. 21, 1986

[51] Int. Cl.⁴ .............................................. A61F 5/04
[52] U.S. Cl. ................................. 128/89 R; 128/87 R
[58] Field of Search ..................... 128/87 R, 89 R, 90, 128/DIG. 15, 88

[56] References Cited

U.S. PATENT DOCUMENTS

| | | | |
|---|---|---|---|
| 2,339,515 | 1/1944 | Parcher | 128/87 R |
| 2,486,687 | 11/1949 | Svaetichin | |
| 3,256,880 | 6/1966 | Caypinar | 128/133 |
| 3,528,412 | 9/1970 | McDavid | 128/80 |
| 3,624,745 | 11/1971 | Bowers | 128/93 |
| 3,643,656 | 2/1972 | Young et al. | 128/90 |
| 3,719,187 | 3/1973 | Ulansey | 128/90 |
| 3,786,805 | 1/1974 | Tourin | 128/87 R |
| 4,019,504 | 4/1977 | Sterling | 128/DIG. 15 X |
| 4,050,455 | 9/1977 | Smith | 128/80 F |
| 4,169,467 | 10/1979 | Rabischong et al. | 128/80 G |
| 4,182,320 | 1/1980 | Sweeney | 128/89 R |

Primary Examiner—Robert A. Hafer
Assistant Examiner—Kathleen J. D'Arrigo
Attorney, Agent, or Firm—Richard C. Woodbridge

[57] ABSTRACT

A modular splint system includes segments that are connectable to each other with a velcro ®-like material. Multiple segments can be connected to each other so as to form an elongated splint. Normally two elongated multi-segment sections are placed on opposite sides of a broken limb and are connected firmly to each other by a strap that engages the velcro ®-like material on the backside of the splint segments. An inflatable air cushion is located on the inside of each splint segment. The air bag may be filled with a coolant in order to reduce swelling and the like. All the components of the splint system and can be stored in a relatively small travelling case.

6 Claims, 13 Drawing Figures

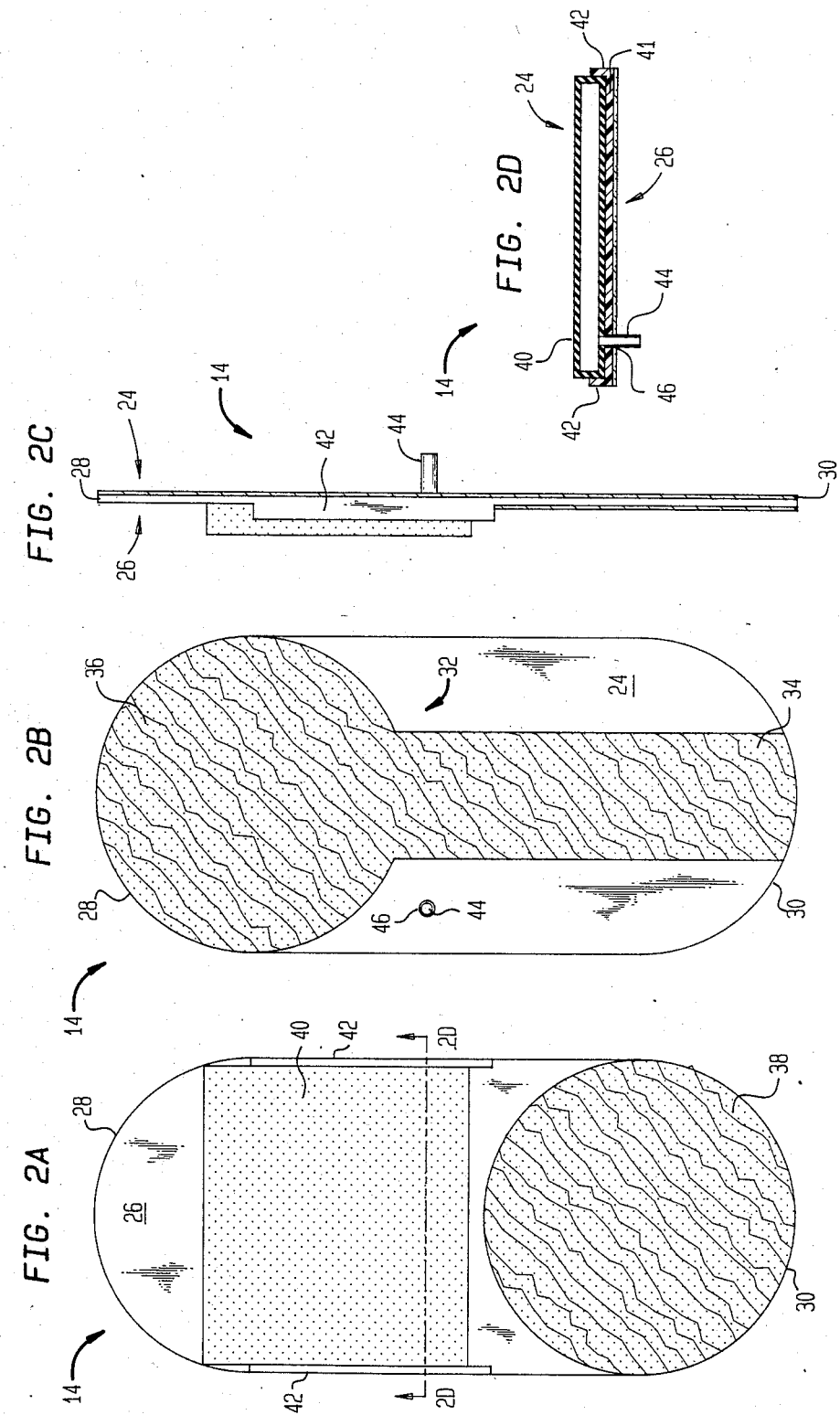

MODULAR SPLINT SYSTEM

BACKGROUND OF THE INVENTION

1. Field of the Invention

The invention relates to an emergency splint formed from modular segments that can be selectively connected to each other and then attached to a broken limb with straps.

2. Description of Related Art

The prior art reveals several attempts to make splints in sections. For example, U.S. Pat. No. 4,019,504 discloses a two section splint having portions which are adjustable with respect to each other. Velcro ® straps are employed to attach the segmented sections to the disabled limb. Velcro ® is a registered trademark of Velcro, Inc., 406 Brown Ave., Manchester, N.H. 03101. Rubber strips on the backside of the splint sections help to increase traction. A wing nut is employed to immobilize the two sections once they are connected together.

A variety of other segmented splints are described in various other U.S. patents. For example, U.S. Pat. No. 4,050,455 discloses a three-section foot and leg splint. Similarly, U.S. Pat. No. 2,486,687 discloses an angulated segmented splint. A three-piece intravenous arm board is disclosed in U.S. Pat. No. 3,256,880. A disposable splint including an extension is disclosed in U.S. Pat. No. 3,624,745.

The use of Velcro ® is noted in some of U.S. patents, including U.S. Pat. No. 3,528,412. U.S. Pat. No. 4,169,467 is of interest in that it discusses the use of a segmented splint employing Velcro ® and air inflation features. Lastly, U.S. Pat. Nos. 3,643,656; 3,786,805 and 4,182,320 disclose prior art splints or casts which are at least partially inflatable.

Several different types of disposable splints are available commercially. Cardboard splints with or without padding are available from Rescue Services, Inc. A disposable inflatable Puff splint is available through the School Health Catalog. Also available from the same organization is a multi-purpose disposable splint No. 20-029 adapted for adult and child leg or arm injuries.

SUMMARY OF THE INVENTION

Briefly described the invention comprises a modular splint including segments that are connectable to each other with a Velcro ®-like material. The entire splint system is preferably packaged in a carrying case containing 8 splints, 4 cans of refrigerant gas, and 8 straps. A typical case might include 6 twelve inch splint segments and 2 eight inch segments. The twelve inch segments are useful for setting long bones, such as found in the arms and legs, whereas the shorter eight inch sections are useful for immobilizing hands and feet. The top of each splint segment typically includes a large, circular, five inch diameter hook portion and an extended narrower two inch strip of hook material having an overall keyhole-like shape. Each bottom section includes a five inch diameter loop fastener target adapted to mate with the hook fastener material on the top side of another splint segment. An inflatable air bag is also located on the bottom side of each splint segment. Multiple splint segments can be connected together by mating the hook material on the top surface with the loop material on the bottom surface of another splint segment. Normally two elongated multi-segment sections are formed in the fashion just described and then placed on opposite sides of a broken limb. A plurality of Velcro ® covered straps are then employed to hold the splint sections in position. Each Velcro ® covered strap engages with the two inch strip on the top surface of the splint segment as well as with itself. By overlapping the splint segments with respect to each other it is possible to form a substantially . continuous air bag cushion along the length of the disabled limb. After the two elongated multi-segment, sections are connected to each other by straps, the air bag portions are inflated to further immobilize the limb and minimize angulation.

These and other features of the invention will be more fully understood by reference to the following drawings.

BRIEF DESCRIPTION OF THE DRAWINGS

FIG. 2A is a bottom plan view of a typical twelve inch long modular splint segment according to the preferred embodiment of the invention.

FIG. 2B is a top plan view of the splint segment illustrated in FIG. 2A.

FIG. 2C is a left side elevational view of the splint segment illustrated in FIG. 2A.

FIG. 2D is a cross-sectional view of the modular splint segment illustrated in FIG. 2A.

DETAILED DESCRIPTION OF THE INVENTION

During the course of this description like numbers will be used to identify like elements according to the different views that illustrate the invention.

Figure 1:
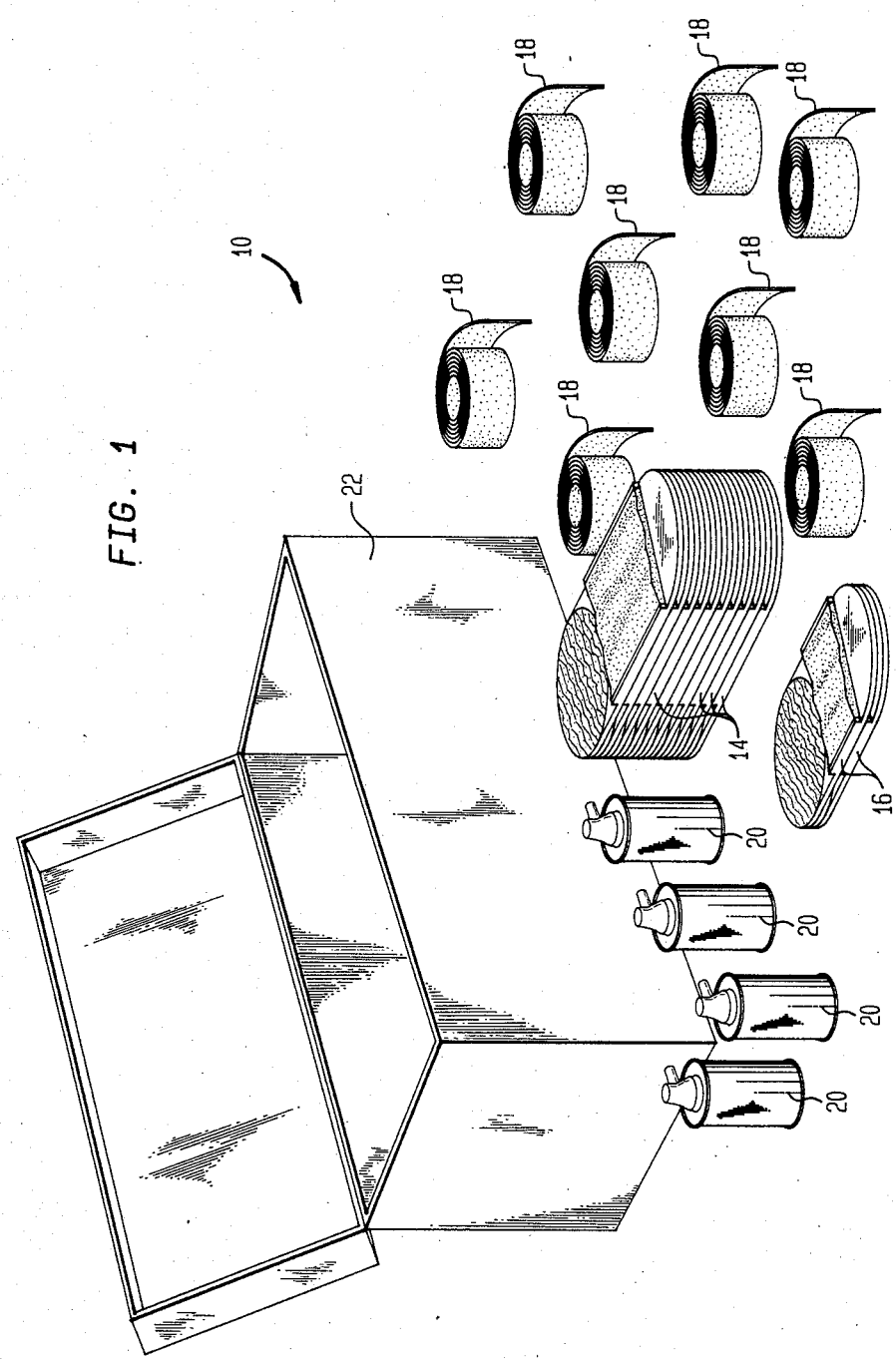
FIG. 1 illustrates the preferred embodiment of the universal module splint system invention and the carrying case in which it is normally found.

The universal splint system 10, according to the preferred embodiment of the invention is illustrated in FIG. 1. The system 10 preferably comprises 6 twelve inch splint segments 14. Two eight inch splint segments 16, 8 straps 18 and 4 cans of refrigerant gas 20. Case 22 is preferably about eighteen inches long, seven inches wide and ten inches high.

Details of the twelve inch splint segment 14 are illustrated in FIGS. 2A–2D. Each modular segment is five inches in width and can vary in length from six inches to twelve inches, with twelve inches being the preferred size. A typical splint segment 14 includes a top surface 24, a bottom surface 26, a first rounded end 28 and a second rounded end 30. Hook fastener Velcro ® material 32 includes two portions 34 and 36 arranged with a keyhole-like shaped configuration. Top portion 36 has a diameter of approximately five inches which coincides with the diameter of the rounded portion 28 of the first end of splint segment 14. The five inch diameter section 36 is connected to a two inch wide section 34 which extends to the second rounded end 30 of the splint segment 14. A five inch diameter section of Velcro ® material 38 having loop fasteners is located on the bottom surface 26 of splint segment 14. Hook fasteners 36 are adapted to mate with the loop fasteners 38 so a plurality of splint segments 14 can be connected together to form elongated, multi-segment sections. An inflatable air bag or cushion 40 is also located on bottom surface 36 and positioned between Velcro ® loop section 38 and the first rounded end 28 of splint segment 14. Inflatable air bag 40 is also located between rigid sidewalls 42. The generally U-shaped cross-section of the splint 14 including the two upstanding sidewalls 42, give the splint segment 14 substantial additional rigidity and strength that it would not have if it were merely a flat piece of material. Sidewalls 42 also serve to provide protection for the inflatable air cushion 40. Air bag 40 is preferably about one-half inch thick when inflated. It rises about one-quarter of an inch above the edge of sidewall 42 which itself is approximately one-quarter of an inch high. A one-way valve 44 is used to inflate air cushion 40. Inflation may be accomplished orally or through the use of refrigerant gas bottles 20. An aperture 46 in splint segment 14 permits the nozzle 44 to extend above the top surface 24. According to the preferred embodiment of the invention, each sidewall 42 is approximately four and one-half inches long and set back by two and a half inches from the top of the rounded end 28. When the foregoing dimensions are combined with the five inch dimension of the loop material 38, the overall length of the segment 14 becomes twelve inches. Each splint 14 including the two sidewalls 42 is preferably made from a plastic material. A variety of known plastic materials such as ABS, polycarbonate and polystyrene would be acceptable. Inflatable air cushion 40 is preferably formed from a soft vinyl plastic and generally has a square shape confined and defined by vertical sidewalls 42.

Figure 2E:
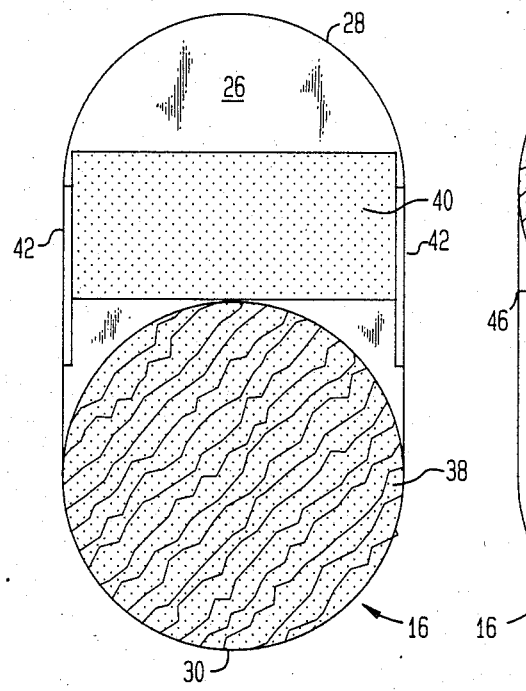
FIG. 2E is a bottom plan view of a smaller eight inch splint segment.
Figure 2F:
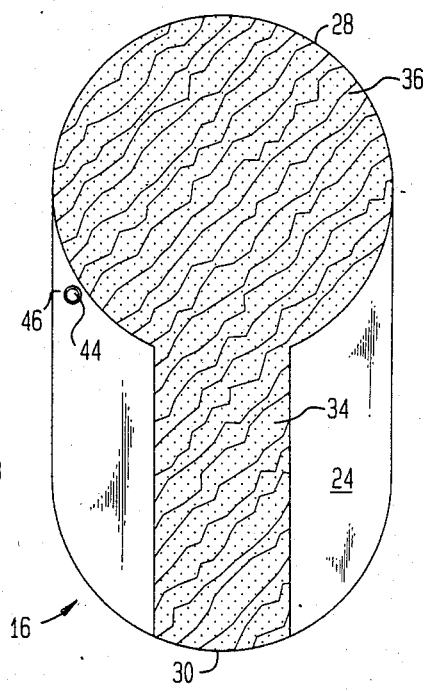
FIG. 2F is a top plan view of the smaller eight inch splint segment illustrated in FIG. 2E.

An eight inch splint segment 16 is illustrated in detail in FIGS. 2E and 2F. The width of eight inch segment 16 is preferably five inches, which is the same as the width of the longer twelve inch sections 14. However, the length of the inflatable air cushion section 40 is diminished in order to decrease the overall length of the splint 16. Except for the decrease length of the splint 16, it is otherwise identical in structure and materials to the longer twelve inch segment 14. As previously described the splint segments preferably vary in length from six inches to twelve inches. Smaller splint segments such as described in FIGS. 2E and 2F are generally employed to protect smaller extremeties, such as hands and feet.

One special feature of the invention is that air bag cushioning is preferably not located in the vicinity where adjacent splint segments 14 and/or 16 overlap each other. This is important because it may be desirable not to place pressure, from an air bag or otherwise, on the injury location. Since the splint segments 14 and/or 16 naturally change direction when applied around a joint, it is virtually impossible to inadvertently put additional pressure on a fracture site.

FIGS. 3A through 3E show the steps typically taken when the splint system 10 is employed to immobilize an injured leg 12.

Figure 3A:
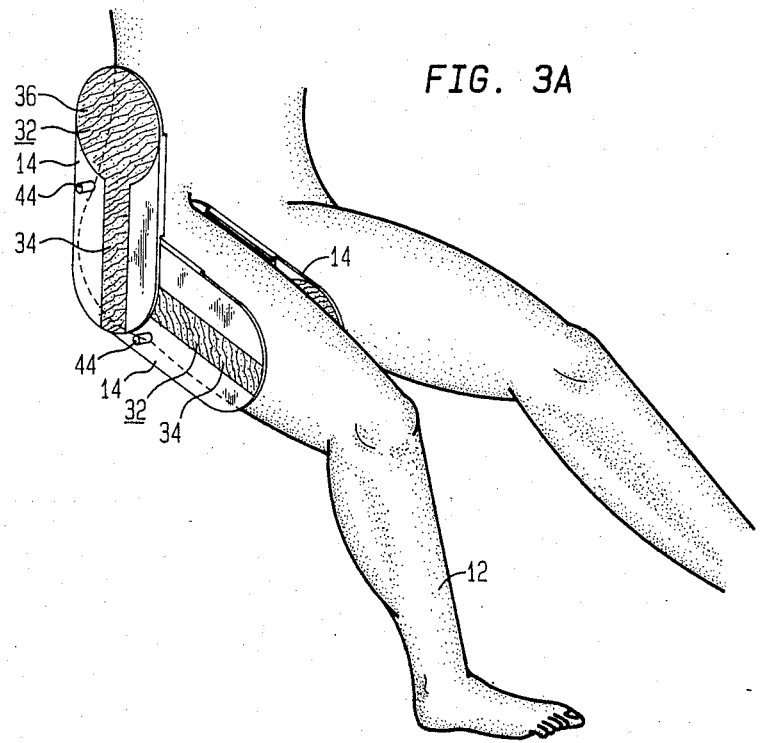
FIGS. 3A through 3E illustrate the typical steps employed to assemble a modular splint according to the preferred embodiment of the system around a fractured leg.

The first step, as shown in FIG. 3A is to place splint segments 14 on opposite sides of the injured leg member 12. Note in FIGS. 3A and 3B that the length of the outside multi-segment section can be longer than the length of the inside multi-segment section. The outside multi-segment section shown in FIG. 3B includes an additional segment 14 that extends above the pelvis of the victim 14 whereas the inside multi-segment section naturally stops at the crotch of the victim.

Figure 3B:
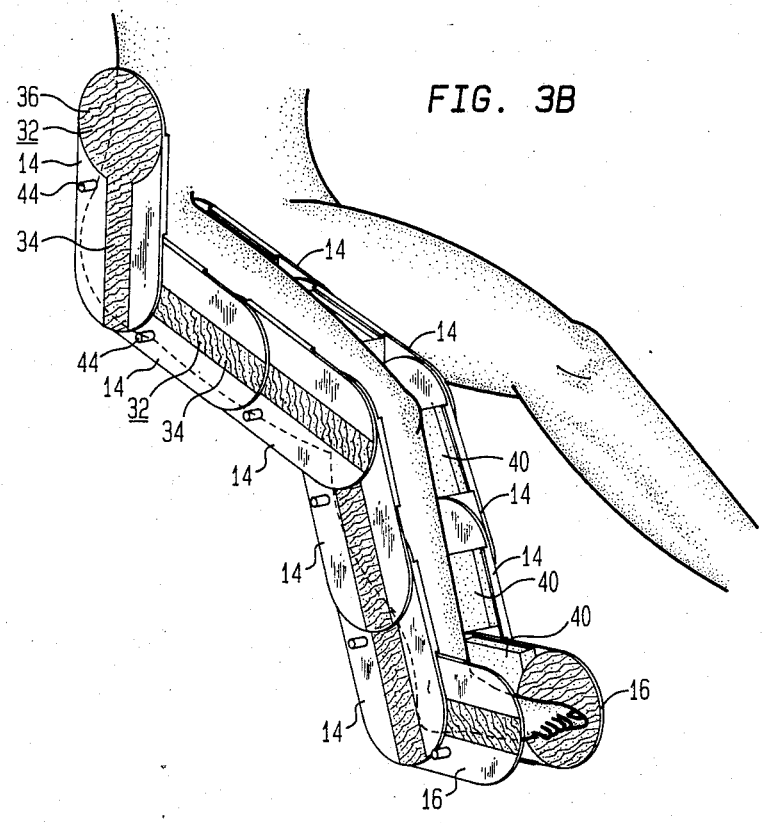
Figure 3C:
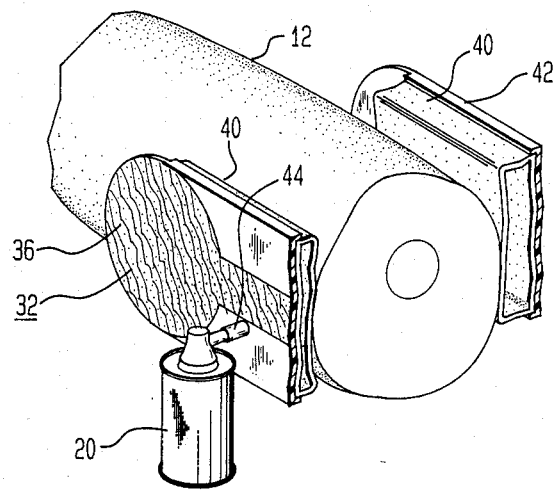

The second step in the process as shown in FIG. 3B is to connect together as many splint segments 14 and 16 as are necessary to complete two multi-segment sections. In the case of a severely broken leg 12 the doctor, trainer, or paramedic might use 5 twelve inch segments 14 and 1 eight inch segment 16 to form the outside multi-segment section. The inside multi-segment section is shown as being formed by 4 twelve inch segments 14 amd 1 eight inch segment 16. The eight inch segments 16 are located on opposite sides of the foot, whereas the longer twelve inch segments 14 are employed to protect the longer bones of the leg 12 and the pelvic region.

The third step in the process is to partially inflate air cushions 40 to between 50 and 80% of full capacity. Air cushions 40 are preferably attached to the splint segments 14, but might, alternatively, be provided separately so that they can be selectively placed in position as appropriate. The purpose of partially inflating the air cushions 40 during the initial stage is to provide comfort and support to the injured limb 12 prior to fine tuning the system 10 in the last step to be described later. If the leg 12 does not exhibit substantial external damage, then it is adequate to inflate the air cushions 40 orally. However, should the leg 12 show substantial swelling or evidence of contusions, then refrigerant gas from canister 20 would preferably be employed to control the swelling and reduce pain.

Figure 3D:
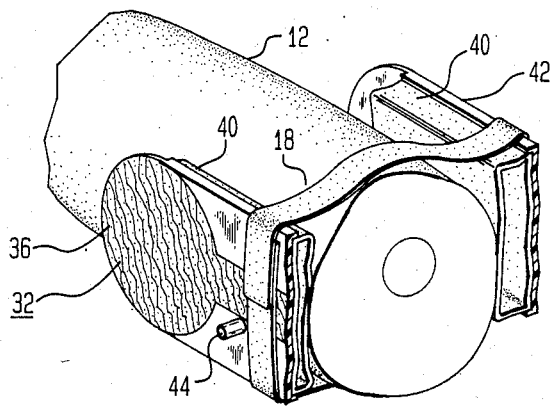

The fourth step as illustrated in FIG. 3D, is to loosely wrap the straps 18 around the two multi-segment sections. Velcro ® straps 18 attach easily to themselves and to the hook fasteners of strip portion 34 of exterior Velcro ® 32. Straps 18 attach to the Velcro ® 32 since the Velcro ® 32 extends the entire length of the multi-segment section. After the initial loose attachment some adjustments are typically made to give the limb 12 additional support.

Figure 3E:
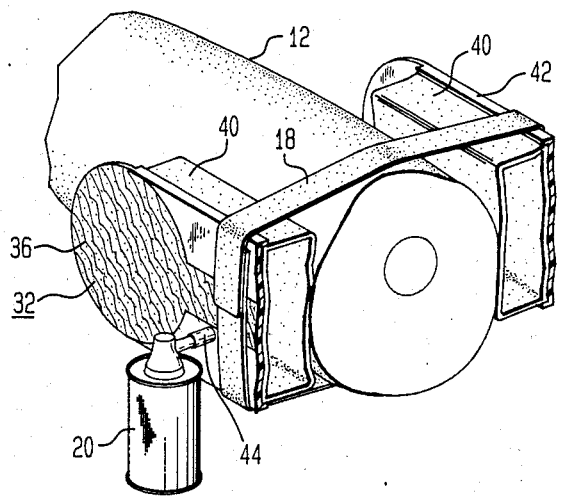

Finally, the fifth step as shown in FIG. 3E is to add additional inflation so as to maximize the immobility of the limb 12. Typically, more refrigerant gas is delivered from the canister 20 so that the splint system 10 is held firmly in place. The victim is now ready for transport to a hospital or a suitable location where further emergency treatment can be administered.

Figure 4:
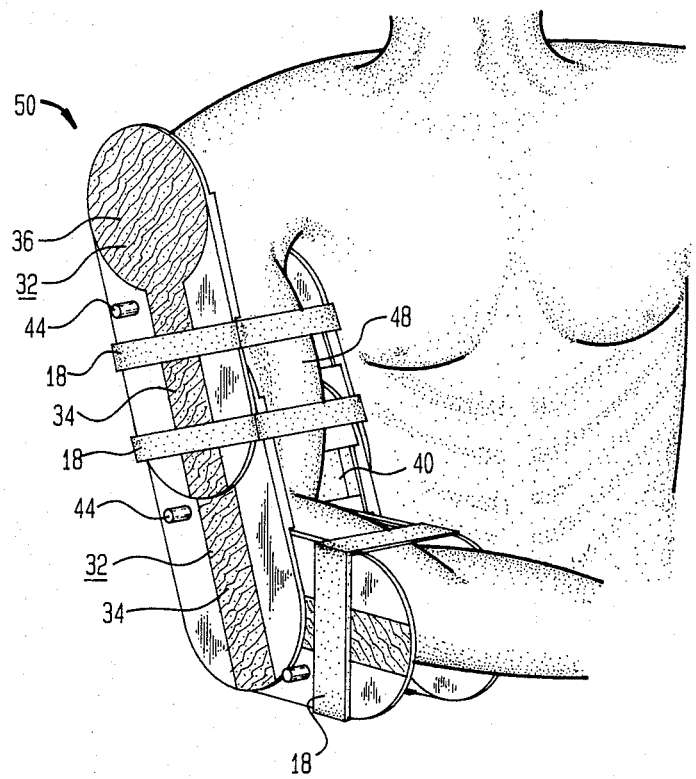
FIG. 4 illustrates the use of the modular splint system on an individual having an arm injury.

One of the major advantages of the present invention lies in its adaptability. The system 10 can be employed to accomodate substantially all arm and leg injuries of varying degrees of seriousness. For example, FIG. 4 illustrates the use of the system 10 in the context of a probable fracture of the upper arm 48.

The invention just described has a number of useful characteristics:

1. It provides rigidity, thereby eliminating unwanted movement of injured and/or tender tissue, bones and joints.

2. The system is especially comfortable for a victim since the use of inflatable air cushions help to minimize discomfort.

3. It is easy to transport the system in compact carrying case 22. Note that the splint segments 14 and 16 can nest one on top of the other in order to minimize space requirements. Each splint segment 14 and 16 is made from a strong, but lightweight plastic. The use of sidewalls 42 increases the overall rigidity of the splint segments 14 and 16 by a factor of at least 3 over flat segments without sidewalls.

4. The system 10 is adaptable to almost any limb position. This is especially important since most prior art splints are directed only towards the most common types of fractures.

5. The splint segments 14 and 16 can be used both on arms and legs.

6. Because the straps 18 connect both to themselves and to the Velcro ® 32 on the splint segments 14 and 16, the complete assembly is connected together very securely.

7. The system 10 is capable of selectively accepting cooling gas from canisters 20 to minimize pain and swelling.

8. The system 10 can be economically manufactured and sold to the public at a very reasonable price.

9. It is relatively easy to keep the elements of the system 10 clean so that they can be reused time and time again.

10. There are presently splints on the market which are air inflatable. Unfortunately, due to their design, they tend to operate in a unilateral direction only, thus forcing angulated injured limbs to straighten when the air splint is inflated. The present system 10 does not force straightening of a twisted limb when such straightening would be undesirable.

While the invention has been described with reference to the preferred embodiment thereof, it will be appreciated by those of ordinary skill in the art that modifications can be made to the structure and materials which form the invention without departing from the spirit and scope thereof.

I claim:

1. A splint apparatus comprising:
   at least a first and second splint segment, each including a segment body having a first and a second side;
   first releasable means located on the first side of each segment body and extending substantially the length of said first side of said segment body;
   second releasable means located on the second side of each segment body for releasably mating with releasable means such as said first releasable means;
   strap means for releasably engaging said first releasable means when said strap means is brought into contact with said first releasable means and for releasably holding onto itself when brought into contact with itself, said first releasable means including a first section for engaging contact with said second releasable means of other splint segments and, a second section for engaging contact with said strap means;
   cushion means attached to said second side of said segment body; and,
   sidewall means connected to said segment body and located on opposite sides of said cushion means and outside the perimeters thereof,
   wherein one of said two releasable means comprises a hook material and the other releasable means comprises a loop material for mating with said hook material.

2. The apparatus of claim 1 wherein said segment body is formed from a substantially rigid plastic material.

3. The apparatus of claim 2 wherein said cushion means comprises an inflatable cushion.

4. A splint segment apparatus for use in forming a multi-segment splint, said splint segment apparatus comprising:
   a segment body having a first and a second side;
   first releasable means located on said first side of said segment body and extending substantially the length of said first side of said segment body;
   second releasable means located on said second side of said segment body for releasably mating with releasable means such as said first releasable means, said first releasable means including a first section for engaging the second releasable means of other splint segments and a second section for engaging contact with a strap;
   cushion means attached to said second side of said segment body; and,
   sidewall means connected to said segment body and located on opposite sides of said cushion means and outside the perimeters thereof,
   wherein one of said two releasable means comprises a hook material and the other of said releasable means comprises a loop material for mating with said hook material.

5. The apparatus of claim 4 wherein said segment body is formed from a substantially rigid plastic material.

6. The apparatus of claim 5, wherein said cushion means comprises an inflatable cushion.

* * * * *